United States Patent [19]

Aberg et al.

[11] Patent Number: 4,556,664
[45] Date of Patent: Dec. 3, 1985

[54] METHOD AND COMPOSITION FOR THE TREATMENT OF CARDIAC ARRHYTHMIAS

[75] Inventors: Gunnar A. K. Aberg, 519 Bergen St., Lawrenceville, N.J. 08648; Peter R. Maroko, Cherry Hill, N.J.; Bo T. af Ekenstam, Hjalteby, Sweden

[73] Assignee: Gunnar A. K. Aberg, Lawrenceville, N.J.

[21] Appl. No.: 588,955

[22] Filed: Mar. 13, 1984

[51] Int. Cl.$^4$ ............................................. A61K 31/445
[52] U.S. Cl. ...................................... 514/330; 514/821
[58] Field of Search .......................... 424/267; 546/225; 514/330, 821

[56] References Cited

U.S. PATENT DOCUMENTS

| | | | |
|---|---|---|---|
| 2,792,399 | 5/1957 | Ekenstam et al. | 260/399 |
| 2,799,679 | 8/1978 | Ekenstam et al. | 260/294 |
| 3,810,986 | 5/1974 | Ekenstam et al. | 424/267 |
| 3,862,321 | 1/1975 | Adams et al. | 424/274 |
| 3,950,422 | 4/1976 | Kaplan | 424/316 |
| 4,110,331 | 8/1978 | Pettersson | 546/225 |
| 4,210,670 | 7/1980 | Cooke | 424/324 |
| 4,302,465 | 11/1981 | Ekenstam et al. | 546/225 |

FOREIGN PATENT DOCUMENTS 161236  11/1957  Sweden.
164063  7/1958  Sweden.

OTHER PUBLICATIONS

Chem. Abst. 76: 81348p (1972)–Tullar.
Chem. Abst. 82: 132713n (1975)–Goehl et al.
Chem. Abst. 95: 62003y (1981)–Ekenstam.
Chem. Abst. 96: 115454a (1982)–Dennhardt.

*Primary Examiner*—Douglas W. Robinson
*Attorney, Agent, or Firm*—Lerner, David, Littenberg, Krumholz & Mentlik

[57] ABSTRACT

A method and pharmaceutical composition are disclosed for treating cardiac arrhythmias employing as an active ingredient at least one compound selected from piperidine-2-carboxylic acid-2,6-dimethyl anilide; piperidine-2-carboxylic acid-2,4-dimethyl anilide; piperidine-2-carboxylic acid-2,4,6-trimethyl anilide; and piperidine-2-carboxylic acid-2-methyl-5-chloro anilide.

20 Claims, No Drawings

METHOD AND COMPOSITION FOR THE TREATMENT OF CARDIAC ARRHYTHMIAS

BACKGROUND OF THE INVENTION

The present invention relates to a method and composition for treating cardiac arrhythmias. More particularly, the invention relates to the treatment of cardiac arrhythmias with at least one compound selected from piperidine-2-carboxylic acid-2,6-dimethyl anilide; piperidine-2-carboxylic acid-2,4-dimethyl anilide; piperidine-2-carboxylic acid-2,4,6-trimethyl anilide; and piperidine-2-carboxylic acid-2-methyl-5-chloro anilide.

The compound piperidine-2-carboxylic acid-2,6-dimethyl anilide is known in the prior art. For example, Ekenstam et al. U.S. Pat. No. 4,302,465 discloses piperidine-2-carboxylic acid-2,6-dimethyl anilide as an intermediate for use in making of, e.g., N-(2-hydroxyethyl)-pipecolinyl-2,6-dimethyl anilide. The latter compound is disclosed in Ekenstam et al. Swedish Pat. No. 161,236 as having antiarrhythmic activity, but piperidine-2-carboxylic acid-2,6-dimethyl anilide is not disclosed as possessing such activity. Other patents disclosing piperidine-2-carboxylic acid-2,6-dimethyl anilide include Pettersson U.S. Pat. No. 4,110,331 and Swedish Pat. Nos. 161,236 and 164,063. However, none of these patents disclose or suggest the use of piperidine-2-carboxylic acid-2-6-dimethyl anilide; piperidine-2-carboxylic acid-2,4-dimethyl anilide; piperidine-2-carboxylic acid-2,4,6-trimethyl anilide; piperidine-2-carboxylic acid-2-methyl-5-chloro anilide in the treatment of cardiac arrhythmias.

The compounds N-methyl-piperidine-2-carboxylic acid-2,6-dimethyl anilide; N-ethyl-piperidine-2-carboxylic acid-2,6-dimethyl anilide; and N-butyl-piperidine-2-carboxylic acid-2,6-dimethyl anilide have also been disclosed as having local anesthetic properties. However, these compounds have serious side effects which make them unsuitable for use as antiarrhythmic agents in man.

SUMMARY OF THE INVENTION

It has now unexpectedly been found that the compounds piperidine-2-carboxylic acid-2,6-dimethyl anilide; piperidine-2-carboxylic acid-2,4-dimethyl anilide; piperidine-2-carboxylic acid-2,4,6-trimethyl anilide; or/and piperidine-2-carboxylic acid-2-methyl-5-chloro anilide have very advantageous properties useful in the treatment of cardiac arrhythmias. These compounds have been found to prevent, inhibit or decrease the frequency of cardiac arrhythmias in conscious coronary-ligated dogs. In particular, it has been found that the compound piperidine-2-carboxylic acid-2,6-dimethyl anilide surprisingly provides a long duration of decreased frequency of arrhythmic heart beats in conscious dogs with ischemia-induced arrhythmias, without causing cardiovascular or CNS side effects. This compound, moreover, has been found to provide activity of surprisingly long duration when administered orally. By contrast, N-methyl-piperidine-2-carboxylic acid-2,6-dimethyl anilide; N-butyl-piperidine-2-carboxylic acid-2,6-dimethyl anilide, or N-ethyl-piperidine-2-carboxylic acid-2,6-dimethyl anilide offered an antiarrhythmic effect that was of short duration and that was accompanied by cardiovascular side effects such as decreased cardiac contractile force and CNS side effects such as convulsions. Moreover, piperidine-2-carboxylic acid-2,6-dimethyl anilide was found to have a significantly higher $LD_{50}$ value after intravenous administration than the other N-alkylated compounds discussed above.

In the body, piperidine-2-carboxylic acid-2,6-dimethyl anilide can be metabolized to form piperidine-2-carboxylic acid-2,6-dimethyl-4-hydroxy-anilide, which is less active as an antiarrhythmic agent than piperidine-2-carboxylic acid-2,6-dimethyl anilide. The para-hydroxylation in the body can be delayed or inhibited by employing one or more of the compounds piperidine-2-carboxylic acid-2,4-dimethyl anilide; piperidine-2-carboxylic acid-2,4,6-trimethyl anilide; and piperidine-2-carboxylic acid-2-methyl-5-chloro anilide. The compounds piperidine-2-carboxylic acid-2,4- dimethyl anilide; piperidine-2-carboxylic acid-2,4,6-trimethyl anilide; and piperidine-2-carboxylic acid-2-methyl-5-chloro anilide have also been tested and were found to be active as antiarrhythmic agents. Thus, when administered intraveneously to coronary-ligated conscious dogs, piperidine-2-carboxylic acid-2,4-dimethyl anilide; piperidine-2-carboxylic acid-2,4,6-trimethyl anilide; and piperidine-2-carboxylic acid-2-methyl-5-chloro anilide totally abolished the ischemia-induced arrhythmias, while piperidine-2-carboxylic acid-2,6-dimethyl-4-hydroxy anilide decreased the frequency of arrhythmogenic ventricular beats by 40%.

in view of the above, the present invention provides a method for treating cardiac arrhythmias in mammals in which at least one compound selected from piperidine-2-carboxylic acid-2,6-dimethyl anilide, piperidine-2-carboxylic acid-2,4-dimethyl anilide, piperidine-2-carboxylic acid-2,4,6-trimethyl anilide, and piperidine-2-carboxylic acid-2-methyl-5-chloro anilide; an optically active isomer thereof; a pharmaceutically acceptable acid addition salt thereof; and/or a mixture of such compounds is administered to a mammal susceptible to cardiac arrhythmias in an effective amount to inhibit such cardiac arrhythmias.

The present invention also therefore provides a pharmaceutical composition for treating cardiac arrhythmias comprising a pharmaceutically acceptable carrier and at least one compound selected from piperidine-2-carboxylic acid-2,6-dimethyl anilide, piperidine-2-carboxylic acid-2,4-dimethyl anilide, piperidine-2-carboxylic acid-2,4,6-trimethyl anilide, and piperidine-2-carboxylic acid-2-methyl-5-chloro anilide; optically active isomers thereof; a pharmaceutically acceptable acid addition salt thereof; and or mixtures of such compounds. The compound is included in the pharmaceutical composition in an amount effective to inhibit cardiac arrhythmias.

DETAILED DESCRIPTION OF THE INVENTION

The active compounds which are used in the method and pharmaceutical composition of the present invention include piperidine-2-carboxylic acid-2,6-dimethyl anilide; piperidine-2-carboxylic acid-2,4-dimethyl anilide; piperidine-2-carboxylic acid-2,4,6-trimethyl anilide; and piperidine-2-carboxylic acid-2-methyl-5-chloro anilide. These compounds can be used in their racemic form or as their optically active isomers. In addition, pharmaceutically acceptable acid addition salts of such compounds can be employed in the method and composition of the invention. Moreover, mixtures of such compounds, or their salts and/or optically active isomers can also be employed.

The preferred compound for use in the method and pharmaceutical composition of the invention is piperidine-2-carboxylic acid-2,6-dimethyl anilide. Again, this compound can be used in its racemic form or in its optically active d-form or its optically actively active l-form. As noted above, and as shown in the examples which follow, this compound provides particularly advantageous properties in the treatment of cardiac arrhythmias, especially when administered orally.

The compounds piperidine-2-carboxylic acid-2,4-dimethyl anilide; piperidine-2-carboxylic acid-2,4,6-trimethyl anilide; and piperidine-2-carboxylic acid-2-methyl-5-chloro anilide have also been found to provide particularly advantageous properties in the treatment of cardiac arrhythmias with the method and pharmaceutical composition of the invention in that such compounds inhibit or delay the metabolization to the corresponding para-hydroxy forms in the body, which para-hydroxy form is less active as an antiarrhythmic agent. Moreover, piperidine-2-carboxylic acid-2,4-dimethyl anilide; piperidine-2-carboxylic acid-2,4,6-trimethyl anilide; and piperidine-2-carboxylic acid-2-methyl-5-chloro anilide are in themselves very active antiarrhythmic agents.

The compounds employed in the method and pharmaceutical composition of the present invention can be prepared by known techniques. For example, the preparation of piperidine-2-carboxylic acid-2,6-dimethyl anilide is disclosed in U.S. Pat. Nos. 4,110,331 and 4,302,465. Since this compound and its pharmaceutically acceptable acid addition salts and optically active isomers are known in the art, such procedures will not be repeated here.

Swedish Pat. No. 161,236 discloses the preparation of piperidine-2-carboxylic acid-2,6-dimethyl anilide by reacting picolinyl chloride with 2,6-dimethylaniline from which picolinyl-2-carboxylic acid-2,6-dimethyl anilide was obtained. The latter compound was thereafter catalytically hydrogenated to form piperidine-2-carboxylic acid-2,6-dimethyl anilide. By substituting 2,4-dimethylaniline, 2,4,6-trimethylaniline or 2-methyl-5-chloroaniline for 2,6-dimethylaniline in such procedure the corresponding compounds piperidine-2-carboxylic acid-2,4-dimethyl anilide; piperidine-2-carboxylic acid-2,4,6-trimethyl anilide and piperidine-2-carboxylic acid-2-methyl-5-chloro anilide can be prepared.

In the method and pharmaceutical composition of the present invention, piperidine-2-carboxylic acid-2,6-dimethyl anilide; piperidine-2-carboxylic acid-2,4-dimethyl anilide; piperidine-2-carboxylic acid-2,4,6-trimethyl anilide; and piperidine-2-carboxylic acid-2-methyl-5-chloro anilide may be administered in conventional dosage forms, such as a tablet, capsule, elixir, transcutaneous patches, injectible composition or the like along with the pharmaceutically acceptable carrier material. Such carrier materials include conventional carrier materials such as potato starch, saccharose, lactose, sterile water, etc., with the particular carrier material being dependent upon the dosage form desired. The pharmaceutical composition of the invention can also include other conventional adjuvants for such compositions, including lubricants, buffers, or the like.

The method and pharmaceutical composition of the invention preferably employs oral dosage forms; however, parenteral or transcutaneous administrations can also be employed. Multiple, single or divided doses of one or more of these four compounds in amounts of from about 1 to about 1,000 miligrams, preferably from about 50 to about 800 miligrams, one to four times per day, may be administered in dosage forms as described above.

The following examples are intended to illustrate, but not to limit, the method and composition of the invention.

EXAMPLE 1

Piperidine-2-carboxylic acid-2,6-dimethyl anilide was administered in an oral dose of 50 mg/kg body weight to conscious dogs with ischemia-induced arrhythmias produced according to the method of Harris (*Circulation*, 1950, Volume 1, page 13–18). This compound decreased the frequency of arrythmic heart beats from 95% to 0%, without causing cardiovascular or CNS side effects. The duration of the antiarrythmic effect of piperidine-2-carboxylic acid-2,6-dimethyl anilide was in excess of six hours. N-methyl-piperidine-2-carboxylic acid-2,6-dimethyl anilide; N-butyl-piperidine-2-carboxylic acid-2,6-dimethyl anilide; and N-ethyl-piperidine-2-carboxylic acid-2,6-dimethyl anilide when administered intraveneously provided antiarrhythmic activity of very short duration and were accompanied by both cardiovascular side effects such as impaired cardiac contractility (cardiac arrest) and CNS side effects such as convulsions and/or respiratory effects.

The acute toxicity of these same compounds was studied in conscious mice. The $LD_{50}$ values after intravenous administration were 45 mg/kg for piperidine-2-carboxylic acid-2,6-dimethyl anilide, 28 mg/kg for lidocaine, 25 mg/kg for N-ethyl-piperidine-2-carboxylic acid-2,6-dimethyl anilide, 34 mg/kg for N-methyl-piperidine-2-carboxylic acid-2,6-dimethyl anilide, and 9 mg/kg for N-butyl-piperidine-2-carboxylic acid-2,6-dimethyl anilide.

In summary, piperidine-2-carboxylic acid-2,6-dimethyl anilide provided unexpectedly advantageous antiarrhythmic effects with relatively low toxicity and without causing cardiovascular or CNS side effects.

EXAMPLE 2

The compounds piperidine-2-carboxylic acid-2,4-dimethyl anilide; piperidine-2-carboxylic acid-2,4,6-trimethyl anilide; and piperidine-2-carboxylic acid-2-methyl-5-chloro anilide were administered to conscious coronary-ligated dogs with ischemia-induced arrhythmias by the Harris procedure cited above. In a dose of 50 mg/kg body weight given orally, all three compounds totally abolished the ischemia-induced arrhythmias and provided an antiarrhythmic effect for several hours.

EXAMPLE 3

Tablets were prepared by mixing 1000 grams of piperidine-2-carboxylic acid-2,6-dimethyl anilide hydrochloride (m.p. 264°–265° C.) with lactose, potato starch and colloidal silic acid. The mixture was moistened with a 10% solution of gelatin and was granulated through a 12-mesh sieve. After drying, potato starch, talc and magnesium stearate were admixed and the resulting mixture was pressed into tablets (10,000) which contained 100 mg of piperidine-2-carboxylic acid-2,6-dimethyl anilide each. Tablets were provided with a breaking score to give another dose than 100 mg or to give multiple doses thereof when broken.

Similar tablets can be prepared by substituting piperidine-2-carboxylic acid-2,4-dimethyl anilide; piperidine-2-carboxylic acid-2,4,6-trimethyl anilide; or piperidine- 2-carboxylic acid-2-methyl-5-chloro anilide for piperidine-2-carboxylic acid-2,6-dimethyl anilide.

EXAMPLE 4

Coated tablets were prepared by the following procedure. Granules were prepared from piperidine-2-carboxylic acid-2,6-dimethyl anilide hydrochloride (1,000 g), lactose, and an alcoholic solution of polyvinylpyrrolidone. After the drying step, the granules were mixed with talc, potato starch and magnesium stearate. The resulting mixture was pressed into 10,000 tablets being biconvex. The tablets were primarily coated with a 10% alcoholic solution of shellac and thereupon with an aqueous solution containing saccharose (45%), gum arabicum (5%), gelatin (4%) and dye stuff (0.2%). Talc and powdered sugar were used for powdering after the first five coatings. The resulting coating was then coated with a 10% carnauba wax solution in carbon tetrachloride.

EXAMPLE 5

Ampoules containing piperidine-2-carboxylic acid-2,6-dimethyl anilide hydrochloride were prepared by dissolving one gram of the compound, 0.8 grams of sodium chloride, and 0.1 grams of ascorbic acid in a sufficient amount of water to give 100 ml of solution. The solution, which contains 10 mg of active substance in each ml, was used in filling ampoules, which were sterilized by heating at 120° C. for twenty minutes.

Similar ampoules can be prepared by substituting piperidine-2-carboxylic acid-2,4-dimethyl anilide; piperidine-2-carboxylic acid-2,4,6-trimethyl anilide; or piperidine-2-carboxylic acid-2-methyl-5-chloro anilide for piperidine-2-carboxylic acid-2,6-dimethyl anilide.

It will be understood that the embodiments described herein are merely exemplary and that a person skilled in the art may make many variations and modifications without departing from the spirit and scope of the invention. All such modifications and variations are intended to be included within the scope of the invention as defined in the appended claims.

What is claimed is:

1. A method for treating cardiac arrhythmias in mammals comprising administering to a mammal susceptible to cardiac arrhythmias an effective amount to inhibit cardiac arrhythmias of at least one compound selected from

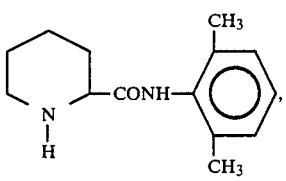

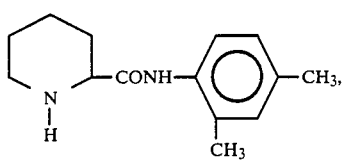

-continued

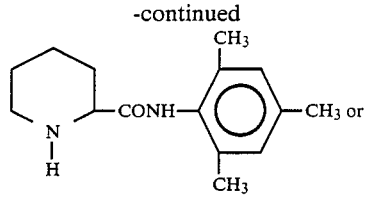

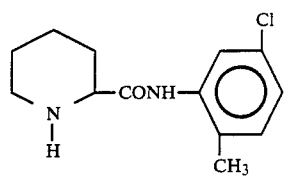

an optically active isomer of such compounds, a pharmaceutically acceptable acid addition salt of such compounds, or mixtures thereof.

2. A method according to claim 1, wherein said compound is

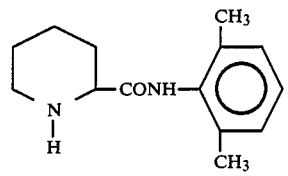

an optically active isomer thereof and/or pharmaceutically acceptable acid addition salt thereof.

3. A method according to claim 2, wherein said compound is administered in its racemic form.

4. A method according to claim 2, wherein said compound is administered in its optically active d-form.

5. A method according to claim 2, wherein said compound is administered in its optically active l-form.

6. A method according to claim 1, wherein said compound is

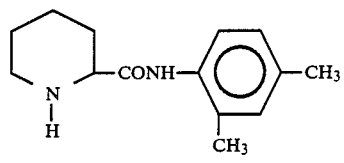

an optically active isomer thereof and/or pharmaceutically acceptable acid addition salt thereof.

7. A method according to claim 1, wherein said compound is

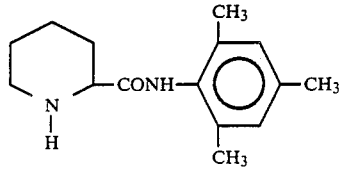

an optically active isomer thereof and/or a pharmaceutically acceptable acid addition salt thereof.

8. A method according to claim 1, wherein said compound is

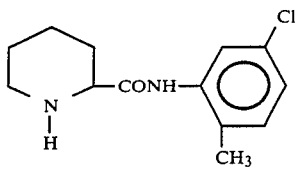

an optically active isomer thereof and/or a pharmaceutically acceptable addition salt thereof.

9. A method according to claim 1, wherein said at least one compound is administered orally.

10. A method according to claim 1, wherein said at least one compound is administered parenterally.

11. A method according to claim 1, wherein said at least one compound is administered at a dosage of from about 50 to about 800 milligrams, one to four times per day.

12. A pharmaceutical composition for treating cardiac arrhythmias in mammals, said composition comprising an effective amount to inhibit cardiac arrhythmias of at least one compound selected from

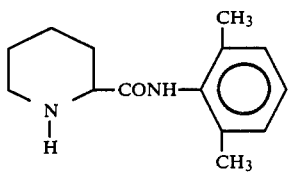

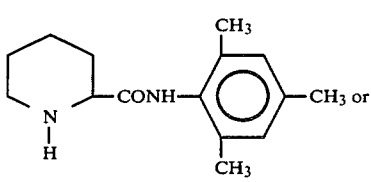

an optically active isomer of such compounds, a pharmaceutically acceptable acid addition salt of such compounds or mixtures thereof, and a pharmaceutically acceptable carrier.

13. A pharmaceutical composition according to claim 12, wherein said compound is an optically active isomer thereof and/or a pharmaceutically acceptable acid addition salt thereof.

14. A pharmaceutical composition according to claim 13, wherein said compound is in its racemic form.

15. A pharmaceutical composition according to claim 13, wherein said compound is in its optically active d-form.

16. A pharmaceutical composition according to claim 13, wherein said compound is in its optically active l-form.

17. A pharmaceutical composition according to claim 12, wherein said compound is

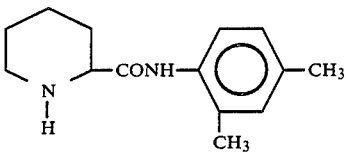

an optically active isomer thereof and/or a pharmaceutically acceptable acid addition salt thereof.

18. A pharmaceutical composition according to claim 12, wherein said compound is

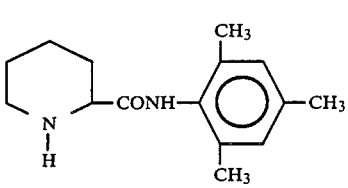

an optically active isomer thereof and/or a pharmaceutically acceptable acid addition salt thereof.

19. A pharmaceutical composition according to claim 12, wherein said compound is

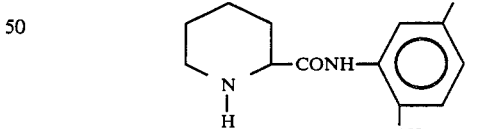

an optically active isomer thereof and/or a pharmaceutically acceptable acid addition salt thereof.

20. A pharmaceutical composition according to claim 12, wherein said at least one compound is contained in said pharmaceutical composition in a dosage unit of from about 50 to about 800 milligrams.

* * * * *